United States Patent [19]

Sweatt

[11] Patent Number: 5,613,854
[45] Date of Patent: Mar. 25, 1997

[54] PLASTIC SLEEVING TO FORM DENTAL COPING AND PONTIC AND METHOD

[76] Inventor: Steven L. Sweatt, 1838 Key Largo Rd., Vista, Calif. 92083

[21] Appl. No.: 423,031

[22] Filed: Apr. 17, 1995

[51] Int. Cl.⁶ .................................. A61C 5/10; A61C 5/08
[52] U.S. Cl. ............................................ 433/223; 433/218
[58] Field of Search ..................................... 433/218, 223, 433/39, 226, 227; 174/DIG. 8; 156/84, 86

[56] References Cited

U.S. PATENT DOCUMENTS

| | | | |
|---|---|---|---|
| 2,989,785 | 6/1961 | Stahl | 156/86 X |
| 3,749,621 | 7/1973 | Shoffner | 156/86 |
| 4,014,724 | 3/1977 | Rausing | 156/86 |
| 4,436,777 | 3/1984 | Karpiloff | 156/84 X |
| 4,576,207 | 3/1986 | Levine et al. | 174/DIG. 8 X |
| 4,624,879 | 11/1986 | Van Dijck et al. | 174/DIG. 8 X |
| 4,802,509 | 2/1989 | Brandolf | 174/DIG. 8 X |
| 4,838,790 | 6/1989 | Koller | 433/219 |
| 4,861,267 | 8/1989 | Shober et al. | 433/218 |
| 4,909,736 | 3/1990 | Ritter | 433/39 |
| 4,940,637 | 7/1990 | Shober et al. | 428/607 |
| 4,976,798 | 12/1990 | Hoffman | 156/86 X |
| 5,134,000 | 7/1992 | Smythe et al. | 174/DIG. 8 X |

*Primary Examiner*—Nicholas D. Lucchesi

[57] ABSTRACT

The method of this invention includes the steps of substituting wax with a new selected medium of a plastic shrinkable material to manufacture a metal substructure known as a dental coping or pontic, for the fabrication of a single or multiple tooth restoration. The new medium is placed over a die, which is the exact replica of what is left of the tooth in a patients mouth that has been clinically prepared for restoration. The die is then covered with the plastic shrink sleeving, and by using an external heat source is shrunk contiguous to the die, leaving a wall thickness of two tenths to three tenths of a millimeter. After trimming away the excess plastic the intermediate plastic is then invested creating a mold which is heated in a high heat oven until the intermediate plastic coping disintegrates completely leaving no unwanted residue on the inner surfaces of the mold. The mold is then cast with a dental alloy to form the metal coping or pontic, upon which the substructures are coated with an acrylic covering or fired on porcelain ceramic compositions to complete the dental restorations.

7 Claims, 1 Drawing Sheet

PLASTIC SLEEVING TO FORM DENTAL COPING AND PONTIC AND METHOD

BACKGROUND OF THE INVENTION

1. Field of the Invention

The present invention relates to the substitutes wax with plastic sleeving plastic sleeving to form dental coping and pontic substructures which act as the support system for several overlays of dental acrylics or porcelains in fabricating a completed dental restoration. A completed restoration is the result of a series of process: first, the plastic; second, the investment to metal; and third, the acrylic or porcelain overlay. Step one, the plastic stage and step two, the "metal stage", will be the focus of this invention.

2. Description of the Prior Art

Forming the coping and pontic structure is a necessary step in the fabrication of dental crowns and bridges. A single tooth that has been clinically prepared by the dentist supports a single coping. A pontic spans between two copings to form a bridge. One or more crowns are constructed upon and supported by a pontic or pontics to replace a tooth or teeth where none exist.

Conventionally, the wax coping and pontic are transformed from wax to metal through the "lost wax" process in which the coping and the pontic are modeled by hand of wax by dipping, flowing, building, layering and hand carving to a precise design and thickness. The wax is sprued, invested, burned out in a high-heat oven and cast in metal in a centrifuge using high fusing alloys. To form a crown for restoring the dentition, the metal coping and pontic is usually covered with a color coating of an acrylic or fired-on porcelain ceramic composition for the purpose of aesthetics as well as function. The metal coping (or pontic) supports the coatings and provides the required structural strength and rigidity for the restored tooth or teeth to resist the force of mastication. The ultimate goal of the conventional wax-to-metal process is to create metal copings and pontics that exactly fit the original clinical preparation. Distortion, expansion, shrinkage, microcracks and impurities are undesirable. Because wax remains unstable, the use of wax causes many of these problems. As evidenced by recent patents, attempts have been made to alter the wax-to-metal process and to even eliminate the lost wax process. Because the materials and processes described in these patents are excessively costly, time consuming and/or non-flexible in design, they have not been accepted in the dental industry as practical alternatives to using wax.

Several methods have been proposed that use metal foil as an alternate to the wax and the lost wax casting method. U.S. Pat. Nos. 4,838,790, 4,861,267 and 490,637 disclose methods of forming a sleeve in which a thin sheet of metal foil is configured to the die. Typically, this sleeve is fused by heating. The metal foil methods have one or more drawbacks. They are time consuming; they are not easily adaptable to all size and shape dies; the results are highly operator dependent; and overlapping metal folds yield variable wall thickness and stress-riser ridges which affect the acrylic or porcelain overlays.

Therefore, the intent of this invention is to introduce a new medium, known as shrink plastic sleeving, for producing copings and pontics intermediate plastic substructures that overcome the shortcomings of the prior art.

It is desirable that the improved coping and pontic intermediate plastic substruct include openings for providing additional gripping attachment of the crown.

Also it is desirable that the improved coping or pontic intermediate plastic substructure include openings to minimize the volume of the coping or pontic intermediate plastic so as to reduce the amount of precious metal used and to increase the amount of acrylic or porcelain overlay material in the perforated areas which aids in aesthetics.

It is also desirable that the volume of the improved coping and pontic intermediate plastic substucture be reduced so as to minimize weight as well as the amount of precious metal used.

SUMMARY OF THE INVENTION

According to a first embodiment of the invention, a plastic sleeve adapted to enclose a model of a clinically prepared tooth, known as a die to the die's margin for forming a dental coping therefrom comprises a sleeve of heat shrink material that has been slipped completely over the die to at least the die's margin and has been shrunk by heating such that the sleeve adjacent the die conforms to the shape of the die. The shrunk sleeve is trimmed to terminate near the die margin. The sleeve material leaves no residue upon its burn-out from an investment casting. The sleeve may have at least one hole therethrough adjacent the outside surface of the die as an aid aesthetics and in attachment of a crown material, such as acrylic or porcelain. The sleeve has substantially uniform wall thickness.

The method of making the sleeve comprises the steps of placing a sleeve of heat shrink material of slightly larger diameter than the die over the die to at least the die's margin and heating the placed sleeve until the sleeve shrinks such that the sleeve adjacent the die conforms to the die's sufaces leaving a wall thickness that varies from one tenth to three tenths of a millimeter; The shrunk sleeve is trimmed at or above the die's margin the die's margin and the shrunk sleeve is pinched flat and trimmed over the die apex.

A method of making an intermediate bridge, comprised of first and second plastic sleeves and a span comprises the steps of forming a plastic first sleeve on a first die, forming a second sleeve on a second die and forming a span or pontic by joining the first and second sleeves with a sleeve span of heat shrink material. Preferably, the span has an opening to the interior such that crown material can enter.

Other features and many attendant advantages of the invention will become more apparent upon a reading of the following detailed description together with the drawings in which like reference numerals refer to like parts throughout.

DETAILED DESCRIPTION OF THE INVENTION

Figure 1:
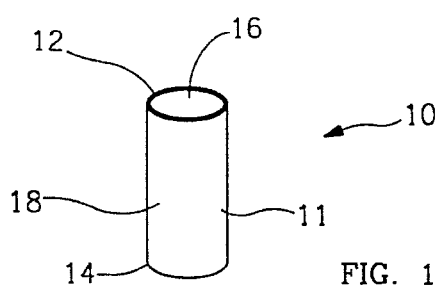
FIG. 1 is a perspective view of a plastic heat shrink sleeve 10 in position for placement over a model 70 including a tooth die 80.

With reference now to the drawings, there is shown in FIG. 1 a perspective view of a plastic heat shrink sleeve 10 in position for placement over a tooth die 80 of a model 70. Sleeve 10 is a plastic heat shrink sleeve that shrinks in circumference with a shrink ratio of about 2:1 to 4:1. A shrink ratio of 2:1 has been found to be preferred. The wall thickness after shrinkage of sleeve 10 may be in the range of 0.20 mm–0.30 mm, with a constant wall thickness of 0.30 mm being preferred. Acceptable, sleeving 10 is commercially available. Other parameters of preferred shrink sleeving will be discussed as they arise.

A typical model 70 includes a base 72, shown as a fragment, supporting a tooth die 80 which is a model of the tooth as prepared in the mouth of the patient. Die 80 includes an outside surface 81, an apex 82 and a margin 84, which delineates the area of die 80 to be covered. Margin 84 is sometimes defined by the top edge of circumferential groove 86. Sleeve 10 includes a wall 11, a top end 12, a bottom end 14, an inside surface 16 and an outside surface 18. Sleeve 10 is of slightly larger diameter than the diameter of die 80. Sleeve 10 should be sufficiently long so as to cover apex 82 of die 80. Preferably, sleeve 10 has a length of about a sleeve diameter longer than the length of die 80. Sleeve 10 is slipped over die 80 such that sleeve bottom end 14 extends past margin 84.

Figure 2:
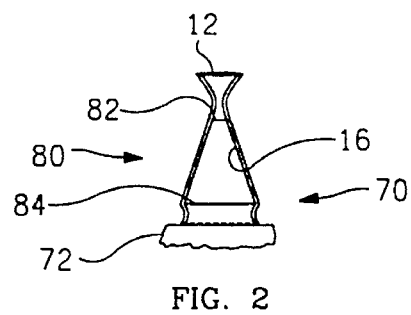
FIG. 2 is a cross-sectional view of the sleeving 10 of FIG. 1 shrunk onto die 80.
Figure 3:
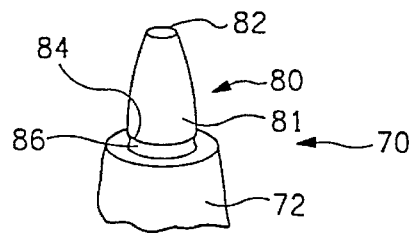
FIG. 3 is a cross-sectional view of sleeve 30 being removed from die 80.

Turning now to FIG. 2, there is shown a cross-sectional view of sleeving 10 of FIG. 1 shrunk onto die 80 by application of an external heat source. To seal over apex 82, sleeve 10 is heated at and above apex 82 and pinched flat and tight over apex 82. Typically, a small piece of the top end 12 of sleeve 10 is pinched off and discarded. Shrunk sleeve 10 is trimmed at or above the margin 84, typically by cutting with a surgical knife to form a dental sleeve 30 as shown in FIG. 3. Inside surface 16 of the remainder of sleeve 10 is now firmly abutting outside surface 81 of die 80.

FIG. 3 is a cross-sectional view of plastic sleeve 30 being removed from die 80. Plastic sleeve 30 is made then into a coping, i.e. a structurally strong member for supporting a crown. Usually a copy, such as of metal, is made of plastic sleeve 30. The lost wax process may be used. Plastic sleeve 30 is sprued, typically at the top, invested and burned out. If this method is used, sleeve 10 should be made of material that will burn out completely and leave no residue. Any residue in the mold results in imperfections in the coping 50 produced. A polymer composition known as pure polyolefin has been found satisfactory for sleeve 10. Sleeve 10 material must be void of any contaminants that will leave residue. This may include some pigments. Because plastic sleeve 30 has a uniform wall thickness and does not distort during investment, the resulting metal coping 50 has a uniform wall thickness and does not require excessive grinding as does copings made from wax.

Figure 4:
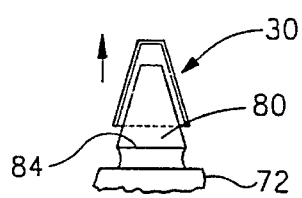
FIG. 4 is a cross-sectional view of the completed crown 60 in position on die 80.

FIG. 4 is a cross-sectional view of a completed crown 60 built up on coping 50 and in position on clinical preparation 80 in a persons mouth.

Figure 5:
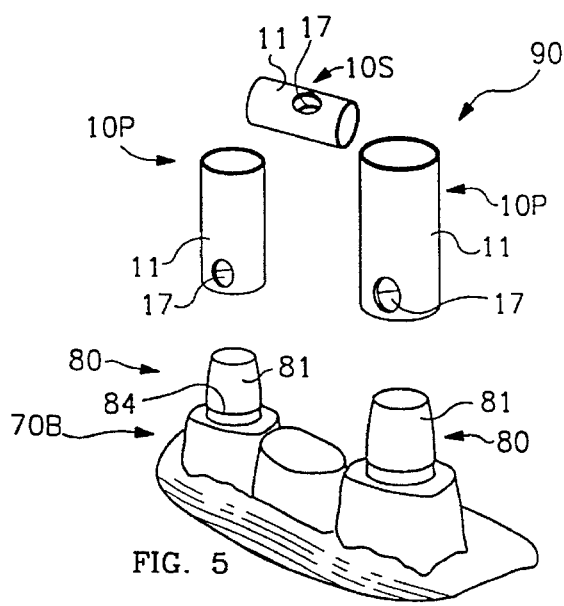
FIG. 5 is a perspective view of an alternate embodiment of the invention showing three perforated heat shrink sleeves 10 in position for forming an intermediate bridge 90.
Figure 6:
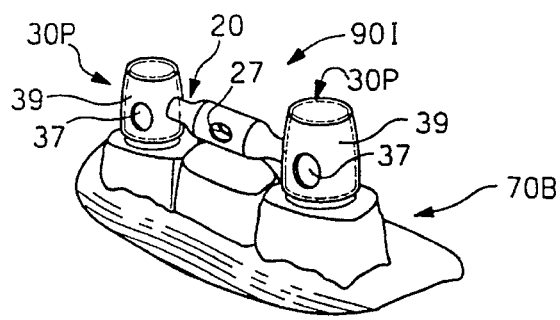
FIG. 6 is a perspective view of intermediate bridge 90 such as formed by the sleeves 10 of FIG. 5.
Figure 7:
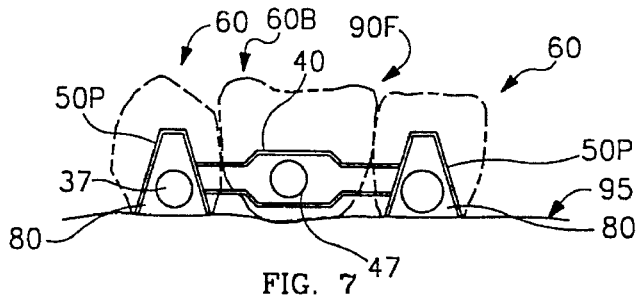
FIG. 7 is a cross-sectional view of finished bridge 90F including crowns 60, including pontic crown 60B, in a person's mouth.

FIGS. 5–7 show the use of heat shrink sleeving 10 in constructing an intermediate bridge 90I for making final bridge 90F and also show the use of perforated sleeving 10P. Although, perforated sleeves 10P and 10S are used to make sleeves 30P and span 20, respectively, and are shown in the construction of intermediate bridge 90I, solid sleeving could also be used.

FIG. 5 is a perspective view of an alternate embodiment of the invention showing three perforated heat shrink sleeves 10P, 10S in position for forming an intermediate bridge 90. A model 70B of a portion of a patient's mouth includes dies 80 and a space therebetween where a tooth is missing. Perforated sleeves 10P include one or more holes or perforations 17 through wall 11. Perforations 17 will increase the thickness of the overlay material as an aid in aesthetics and aid in bonding of crown 60 in that crown material flows into perforation 17 and grips around the edge of perforation 17. In other respects sleeves 10P function the same as solid sleeve 10 of FIGS. 1–3.

Sleeves 10P function the same as sleeve 10 previously described except the perforations are intended to lie over outside surface 81 of die 80. Each sleeve 10P is slid over its respective die 80, shrunk, pinched and margin trimmed to form sleeves 30P as shown in FIG. 6. It is important to the operator that the perforations are introduced prior to the metal stage or lost plastic process as inserting them afterwards is much more difficult.

Perforated span sleeve 10S includes perforations 17 through wall 11. Span sleeve 10S has a length such that it can join sleeves 30P. The ends of span sleeve 10S may be shrunk, as shown, may be trimmed to conform to the outside side wall 39 of sleeve 30P and are attached to the outside side walls 39 of sleeves 30P, such as by heat fusion, molten plastic, glue or wax. Again, if the lost plastic method is used, anything used as glue should not leave any residue.

FIG. 6 is a perspective view of intermediate bridge 90I as formed by the sleeves 10P, 10S of FIG. 5 and removed from mold 70B and includes two plastic end sleeves 30P joined by plastic span 20. Span 20 includes openings 27 to the interior. Plastic sleeves 30P are made then into copings 50P, such as described above. Span 20 is similarly transformed into pontic 40, i.e. a structurally strong member, such as of metal, used to support a crown 60B on bridge 90F. Pontic 40, shown, is hollow with perforation orifices 47 leading to the interior and, therefore, uses far less metal than a solid pontic.

FIG. 7 shows a finished bridge 90F that is made from intermediate bridge 90I in position in a person's mouth. Clinical preparations 80 protrude from jaw and gums, denoted generally as 95. Crowns 60 have been built up on copings 50P and crown 60B has been built up on pontic 40. Importantly, during fabrication, crown material has flowed into perforations in copings 50P so as to enhance esthetics and to better fasten to copings 50P and crown material has flowed into perforation orifices 47 in pontic 40 so as to fill the inside of pontic 40, reducing volume and weight of metal. As a result, crown 60B is more firmly attached to perforated pontic 40 than to a solid pontic.

The invention practically eliminates the wax stage including the thermally controlled heated wax pot, special waxing tools, wax processes requiring labor and the time as well as additional labor and lost time necessitated by the high percentage of rework.

Compared to the conventional method, the plastic sleeves and span of the invention are more quickly and easily made, better retain their original shape in handling and storage and make stronger and less expensive copings and pontics. The plastic sleeve of the invention produces metal copings and pontics that produce a perfect fit every time.

Although particular embodiments of the invention have been illustrated and described, various changes may be made in the form, composition, construction, and arrangement of the parts without sacrificing any of its advantages. Therefore, it is to be understood that all matter herein is to be interpreted as illustrative and not in any limiting sense, and it is intended to cover in the appended claims such modifications as come within the true spirit and scope of the invention.

In the appended claims, the term die defines a working model of an actual clinical preparation in a patient's mouth. The die is an exact copy or duplicate of the preparation and is usually formed from dental gypsum stone.

In the appended claims, the term pontic defines a span between two abutment dies or copings for the purpose of replacing or restoring dentition where no tooth or teeth exist, commonly known in the art as a bridge, A bridge consists of no less than one pontic.

I claim:

1. A method of forming an intermediate plastic coping upon which a restored crown or bridge may be fabricated, comprising the steps of:

(a) placing a sleeve of plastic heat-shrink tubing over a die, said die having a margin, (b) heating said sleeve to a temperature sufficient to cause shrinkage of said sleeve with said sleeve conforming to the surfaces of the die, thus forming a first coping, (c) trimming the coping so that the coping terminates at a height no lower than said margin, (d) removing the coping from the die, (e) investing the coping to prepare a mold for a metal casting, and (f) burning out the coping to create a void into which a metal is then cast in the mold.

2. The method of claim 1, further comprising the step of forming a second plastic coping.

3. The method of claim 1, further comprising the step of placing a length of shrink plastic between said first coping and said second coping and joining said copings to said length of shrink plastic, thus forming an intermediate plastic pontic.

4. The method of claim 1, wherein said tubing comprises a polymeric material.

5. The method of claim 4, wherein said polymeric material is polyolefin.

6. The method of claim 1, wherein said die is a replica of a prepared tooth of a patient.

7. The method of claim 1, further comprising the step of forming a metal coping from said metal and covering said metal coping with an overlay to complete the formation of a dental prosthesis.

* * * * *